(12) United States Patent
Moyer et al.

(10) Patent No.: US 8,439,870 B2
(45) Date of Patent: May 14, 2013

(54) SAFETY NEEDLE ASSEMBLY AND METHODS

(75) Inventors: Scott A. Moyer, Breiningsville, PA (US); Michael J. Janders, Northampton, PA (US)

(73) Assignee: B. Braun Medical Inc., Bethlehem, PA (US)

( * ) Notice: Subject to any disclaimer, the term of this patent is extended or adjusted under 35 U.S.C. 154(b) by 326 days.

(21) Appl. No.: 12/555,523

(22) Filed: Sep. 8, 2009

(65) Prior Publication Data

US 2010/0063455 A1  Mar. 11, 2010

Related U.S. Application Data

(60) Provisional application No. 61/095,716, filed on Sep. 10, 2008.

(51) Int. Cl.
*A61M 5/00* (2006.01)
*A61M 5/178* (2006.01)
*A61M 5/32* (2006.01)

(52) U.S. Cl.
USPC ........... 604/110; 604/164.08; 604/164.12; 604/165.01; 604/174; 604/192; 604/198

(58) Field of Classification Search .......... 604/110, 604/162, 164.08, 164, 12, 165.01, 165, 2, 604/165.03, 165.04, 171, 174, 177, 192, 604/194, 198, 263
See application file for complete search history.

(56) References Cited

U.S. PATENT DOCUMENTS

| 4,316,462 | A | 2/1982 | Baker |
| 4,611,382 | A | 9/1986 | Clark |
| 4,627,843 | A | 12/1986 | Raines |
| 4,664,654 | A | 5/1987 | Strauss |
| 4,762,516 | A | 8/1988 | Luther et al. |
| 4,813,940 | A | 3/1989 | Parry |
| 4,832,696 | A | 5/1989 | Luther et al. |
| 4,834,718 | A | 5/1989 | McDonald |
| 4,892,521 | A | 1/1990 | Laico et al. |
| 4,921,490 | A | 5/1990 | Spier et al. |
| 4,935,012 | A | 6/1990 | Magre et al. |
| 4,986,819 | A | 1/1991 | Sobel |

(Continued)

FOREIGN PATENT DOCUMENTS

EP  1 221 304 A2  7/2002
WO  WO 2006/007556 A2  1/2006

OTHER PUBLICATIONS

International Preliminary Report completed Mar. 15, 2011 and mailed Mar. 24, 2011 from corresponding International Application No. PCT/US2009/056368, filed Sep. 9, 2009 (8 pages).

(Continued)

*Primary Examiner* — Bhisma Mehta
(74) *Attorney, Agent, or Firm* — Klein, O'Neill & Singh, LLP

(57) ABSTRACT

Embodiments of the present safety needle assembly include a slidable needle shield. Digital pressure applied to a leaf spring retention latch removes a compressive force from a biasing member and automatically moves the needle shield from a ready-to-use configuration to a protected configuration in which the needle shield covers the sharp needle tip. In the protected configuration the needle shield is prevented from sliding proximally along the needle a sufficient distance to expose the needle tip.

22 Claims, 9 Drawing Sheets

SECTION A-A

SECTION D-D

U.S. PATENT DOCUMENTS

| | | | |
|---|---|---|---|
| 4,998,922 A | 3/1991 | Kuracina et al. |
| 5,030,212 A | 7/1991 | Rose |
| 5,053,018 A | 10/1991 | Talonn et al. |
| 5,084,030 A | 1/1992 | Byrne et al. |
| 5,084,032 A | 1/1992 | Kornberg et al. |
| 5,088,982 A | 2/1992 | Ryan |
| 5,088,986 A | 2/1992 | Nusbaum |
| 5,092,851 A | 3/1992 | Ragner |
| 5,104,384 A | 4/1992 | Parry |
| 5,112,311 A | 5/1992 | Utterberg et al. |
| 5,120,320 A | 6/1992 | Fayngold |
| 5,151,088 A | 9/1992 | Allison et al. |
| 5,152,751 A | 10/1992 | Kozlowski |
| 5,201,721 A | 4/1993 | Lee et al. |
| 5,232,456 A | 8/1993 | Gonzalez |
| 5,246,428 A | 9/1993 | Falknor |
| 5,266,072 A | 11/1993 | Utterberg et al. |
| 5,292,314 A | 3/1994 | D'Alessio et al. |
| 5,295,975 A | 3/1994 | Lockwood, Jr. |
| 5,300,039 A | 4/1994 | Poulsen |
| 5,300,045 A | 4/1994 | Plassche, Jr. |
| 5,308,332 A | 5/1994 | Dillard, III et al. |
| 5,312,359 A | 5/1994 | Wallace |
| 5,354,281 A | 10/1994 | Chen |
| 5,364,360 A | 11/1994 | Flumene |
| 5,370,628 A | 12/1994 | Allison et al. |
| 5,372,590 A | 12/1994 | Haber et al. |
| 5,389,085 A | 2/1995 | D'Alessio et al. |
| 5,423,766 A | 6/1995 | Di Cesare |
| 5,431,630 A | 7/1995 | Leonard |
| 5,460,611 A | 10/1995 | Alexander |
| 5,462,534 A | 10/1995 | Debreczeni |
| 5,472,430 A | 12/1995 | Vaillancourt et al. |
| 5,492,536 A | 2/1996 | Mascia |
| 5,536,257 A | 7/1996 | Byrne et al. |
| 5,549,572 A | 8/1996 | Byrne et al. |
| 5,573,510 A | 11/1996 | Isaacson |
| 5,573,513 A | 11/1996 | Wozencroft |
| 5,578,053 A | 11/1996 | Yoon |
| 5,582,597 A | 12/1996 | Brimhall et al. |
| 5,601,535 A | 2/1997 | Byrne et al. |
| 5,658,255 A | 8/1997 | Ishak |
| 5,662,610 A | 9/1997 | Sircom |
| 5,688,241 A | 11/1997 | Asbaghi |
| 5,695,476 A | 12/1997 | Harris |
| 5,709,662 A | 1/1998 | Olive et al. |
| 5,720,727 A | 2/1998 | Alexander et al. |
| 5,746,727 A | 5/1998 | Graves et al. |
| 5,749,857 A | 5/1998 | Cuppy |
| 5,772,636 A | 6/1998 | Brimhall et al. |
| 5,795,336 A | 8/1998 | Romano et al. |
| 5,800,404 A | 9/1998 | Poulsen |
| 5,810,775 A | 9/1998 | Shaw |
| 5,833,670 A | 11/1998 | Dillon et al. |
| 5,836,920 A | 11/1998 | Robertson |
| 5,879,337 A | 3/1999 | Kuracina et al. |
| 5,893,845 A | 4/1999 | Newby et al. |
| 5,899,886 A | 5/1999 | Cosme |
| RE36,398 E | 11/1999 | Byrne et al. |
| RE36,447 E | 12/1999 | Byrne et al. |
| 5,997,513 A | 12/1999 | Smith et al. |
| 6,004,296 A | 12/1999 | Jansen et al. |
| 6,030,366 A | 2/2000 | Mitchell |
| 6,059,758 A | 5/2000 | Padilla et al. |
| 6,077,253 A | 6/2000 | Cosme |
| 6,149,629 A | 11/2000 | Wilson et al. |
| 6,156,013 A | 12/2000 | Mahurkar |
| 6,159,184 A | 12/2000 | Perez et al. |
| 6,171,283 B1 | 1/2001 | Perez et al. |
| 6,190,361 B1 | 2/2001 | Gettig et al. |
| 6,193,696 B1 | 2/2001 | Jansen et al. |
| 6,235,006 B1 | 5/2001 | Dillon et al. |
| 6,280,420 B1 | 8/2001 | Ferguson et al. |
| 6,298,541 B1 | 10/2001 | Newby et al. |
| 6,302,868 B1 | 10/2001 | Mohammad |
| 6,379,337 B1 | 4/2002 | Mohammad |
| 6,436,086 B1 | 8/2002 | Newby et al. |
| 6,440,104 B1 | 8/2002 | Newby et al. |
| 6,500,155 B2 | 12/2002 | Sasso |
| 6,558,402 B1 | 5/2003 | Chelak et al. |
| 6,592,556 B1 | 7/2003 | Thorne |
| 6,595,955 B2 | 7/2003 | Ferguson et al. |
| 6,613,022 B1 | 9/2003 | Doyle |
| 6,635,032 B2 | 10/2003 | Ward, Jr. |
| 6,638,256 B2 | 10/2003 | Jansen et al. |
| 6,648,855 B2 | 11/2003 | Crawford et al. |
| 6,659,983 B2 | 12/2003 | Crawford et al. |
| 6,659,984 B2 | 12/2003 | Crawford et al. |
| 6,673,047 B2 | 1/2004 | Crawford et al. |
| 6,679,864 B2 | 1/2004 | Gagnieux et al. |
| 6,699,217 B2 | 3/2004 | Bennett et al. |
| 6,719,730 B2 | 4/2004 | Jansen et al. |
| 6,743,186 B2 | 6/2004 | Crawford et al. |
| 6,796,968 B2 | 9/2004 | Ferguson et al. |
| 6,855,129 B2 | 2/2005 | Jensen et al. |
| 6,855,130 B2 | 2/2005 | Saulenas et al. |
| 6,872,194 B2 | 3/2005 | Doyle et al. |
| 6,926,696 B2 | 8/2005 | Mohammed |
| 6,981,965 B2 | 1/2006 | Luther et al. |
| 6,984,223 B2 | 1/2006 | Newby et al. |
| 6,994,213 B2 | 2/2006 | Giard, Jr. et al. |
| 6,997,913 B2 | 2/2006 | Wilkinson |
| 7,001,363 B2 | 2/2006 | Ferguson et al. |
| 7,008,402 B2 | 3/2006 | Ferguson et al. |
| 7,014,623 B2 | 3/2006 | Prestidge et al. |
| 7,037,294 B2 | 5/2006 | Luther et al. |
| 7,083,600 B2 | 8/2006 | Meloul |
| 7,101,355 B2 | 9/2006 | Doyle |
| 7,118,552 B2 | 10/2006 | Shaw et al. |
| 7,128,726 B2 | 10/2006 | Crawford et al. |
| 7,144,388 B2 | 12/2006 | Crawford |
| 7,198,617 B2 | 4/2007 | Millerd |
| 7,198,618 B2 | 4/2007 | Ferguson et al. |
| 7,201,740 B2 | 4/2007 | Crawford |
| 7,223,258 B2 | 5/2007 | Crawford |
| 7,294,118 B2 * | 11/2007 | Saulenas et al. ............ 604/110 |
| 7,300,420 B2 | 11/2007 | Doyle |
| 7,316,668 B2 | 1/2008 | Swenson |
| 7,354,422 B2 | 4/2008 | Riesenberger et al. |
| 7,422,573 B2 | 9/2008 | Wilkinson et al. |
| 7,428,773 B2 | 9/2008 | Newby et al. |
| 7,691,083 B2 | 4/2010 | Botich et al. |
| 2003/0032927 A1 | 2/2003 | Halseth et al. |
| 2005/0119627 A1 | 6/2005 | Crawford |
| 2005/0177112 A1* | 8/2005 | Restelli et al. ............ 604/177 |
| 2006/0079847 A1 | 4/2006 | Crawford |
| 2006/0271001 A1 | 11/2006 | Hirota et al. |
| 2007/0060841 A1 | 3/2007 | Henshaw |
| 2007/0185456 A1* | 8/2007 | Nakajima ............ 604/164.08 |
| 2008/0119795 A1 | 5/2008 | Erskine |
| 2008/0167619 A1 | 7/2008 | Tanaka et al. |
| 2009/0254042 A1* | 10/2009 | Gratwohl et al. ............ 604/198 |

OTHER PUBLICATIONS

International Search Report completed Apr. 12, 2010 and mailed Apr. 13, 2010 from corresponding International Application No. PCT/US2009/056368, filed Sep. 9, 2009 (4 pages).

Written Opinion completed Apr. 12, 2010 and mailed Apr. 13, 2010 from corresponding International Application No. PCT/US2009/056368, filed Sep. 9, 2009 (5 pages).

Supplementary European Search Report dated Mar. 13, 2012 from corresponding European Application No. 09813540.3 (12 pages).

* cited by examiner

FIG. 5

FIG. 6
SECTION D-D

FIG. 9
SECTION A-A

FIG. 10
SECTION B-B

FIG. 16 SECTION A-A

FIG. 15 SECTION C-C

FIG. 17 SECTION B-B

FIG. 18

FIG. 19
SECTION D-D

FIG. 20

SAFETY NEEDLE ASSEMBLY AND METHODS

CROSS-REFERENCE TO RELATED APPLICATION

This is a regular utility application of provisional application Ser. No. 61/095,716, filed Sep. 10, 2008, the contents of which are expressly incorporated herein by reference for all purposes.

BACKGROUND

The present invention relates to apparatus and methods for percutaneously infusing fluids to a body and/or withdrawing fluids from a body.

DESCRIPTION OF RELATED ART

Needle assemblies are commonly used to percutaneously infuse fluids to a body and/or withdraw fluids from a body. The needle assembly generally remains disposed in the vasculature while one or more assemblies are connected and disconnected to the assembly to complete the infusion/withdrawal process. Upon withdrawing the assembly from the vasculature, the sharp distal tip of the needle is exposed. It is disadvantageous to leave the tip exposed, as there is a risk that medical staff will accidentally prick themselves. This phenomenon is known as needlestick, and can transfer blood borne diseases.

SUMMARY

The preferred embodiments of the present safety needle assembly and methods have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description of the Preferred Embodiments," one will understand how the features of the present embodiments provide advantages, which include reliable covering of the sharp needle tip.

One embodiment of the present safety needle assembly comprises an elongate body including a body wall defining an internal passageway and including an opening in the body wall. The assembly further comprises a needle hub engaging a proximal end of the body and being stationary with respect to the body. The assembly further comprises a needle extending distally from the needle hub and through the body internal passageway. The needle includes a sharp distal tip. A needle shield is disposed within the body internal passageway and surrounds a portion of the needle. The needle shield is slidable with respect to the body and with respect to the needle. A biasing element engages the needle shield and biases the needle shield toward a distal end of the needle. A release latch extends from the needle shield. The release latch comprises a leaf spring having a detent. When the assembly is in a ready-to-use configuration the detent engages an edge of the opening in the body wall and prevents movement of the needle shield distally with respect to the body and with respect Co the needle. Digital pressure applied to the release latch disengages the detent from the edge of the opening in the body wall and enables movement of the needle shield distally with respect to the body and with respect to the needle.

One embodiment of the present methods of manufacturing a safety needle assembly comprises providing an elongate body including a body wall defining an internal passageway and including an opening in the body wall. The method further comprises engaging a wing with the body such that the wing extends laterally from the body. The wing includes a substantially planar portion configured to lie against a patient's skin for securing the assembly to the patient. The method further comprises engaging a needle hub with a proximal end of the body, such that a needle having a sharp distal tip extends through the body internal passageway and out a distal end of the body. The needle hub is stationary with respect to the body. The method further comprises positioning a needle shield within the body internal passageway such that the shield surrounds a portion of the needle and the shield is slidable with respect to the body and with respect to the needle, but the shield is substantially not rotatable with respect to the body. The method further comprises compressing a biasing element between the needle huh and the needle shield such that the biasing element biases the needle shield toward a distal end of the needle. The method further comprises engaging a release latch extending from the needle shield with an edge of the opening in the body wall such that the release latch prevents movement of the needle shield distally with respect to the body and with respect to the needle.

One embodiment of the present methods of shielding a needle in a safety needle assembly comprises grasping an elongate body of the assembly in a ready-to-use configuration. The elongate body includes a body wall defining an internal passageway and including an opening in the body wall. The internal passageway encloses a portion of a needle having a sharp distal tip. The sharp distal tip extends beyond an open end of the body. The method further comprises depressing a release latch to thereby disengage a detent of the release latch from an edge of the opening in the body wall. Disengagement of the detent from the opening releases a compressive force on a biasing member and causes a needle shield disposed within the body internal passageway to slide distally with respect to the body and with respect to the needle and to cover the needle distal tip. The needle is held in a needle hub that engages a proximal end of the body and is stationary with respect to the body, such that when the release latch is depressed neither the needle nor the needle hub moves with respect to the body.

Another exemplary safety needle assembly provided herein comprises an elongate body including a body wall defining an internal passageway and including an opening in the body wall. A needle hub engages a proximal end of the body and is stationary with respect to the body and having a needle extending distally from the needle hub and through the body internal passageway, the needle includes a sharp distal tip. A needle shield is disposed within the body internal passageway and surrounding a portion of the needle. In an embodiment, the needle shield is slidable with respect to the body and with respect to the needle and having an elongated section having a proximal opening, an internal bore of a first diameter, a release latch comprising a leaf spring extending from the elongated section, and a plurality of proximally extending retention latches each comprising leg and a detent. To move the needle shield, a biasing element is incorporated and engages the needle shield and biasing the needle shield toward a distal end of the needle. Wherein the release latch is engaged to the opening in the body wall to maintain the biasing element in a compressed state.

BRIEF DESCRIPTION OF THE DRAWINGS

The preferred embodiments of the present safety needle assembly and methods now will be discussed in detail with an emphasis on highlighting the advantageous features. These embodiments depict the novel and non-obvious safety needle assembly and methods shown in the accompanying drawings, which are for illustrative purposes only. These drawings include the following figures, in which like numerals indicate like parts.

DETAILED DESCRIPTION OF THE PREFERRED EMBODIMENTS

In the detailed description that follows, the present embodiments are described with reference to the drawings. In the drawings, elements of the present embodiments are labeled with reference numbers. These reference numbers are reproduced below in connection with the discussion of the corresponding drawing features.

Figure 3:
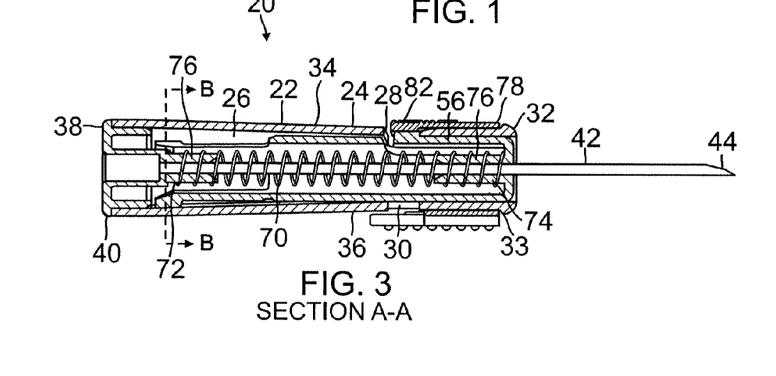
FIG. 3 is a left-side sectional view of the safety needle assembly of FIG. 1, taken through the line A-A in FIG. 1.
Figure 4:
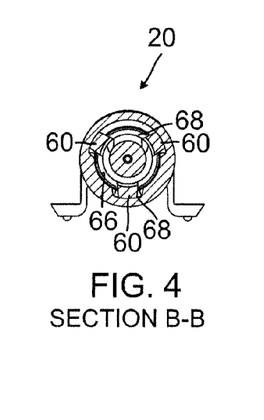
FIG. 4 is a rear sectional view of the safety needle assembly of FIG. 1, taken through the line B-B in FIG. 3.
Figure 5:
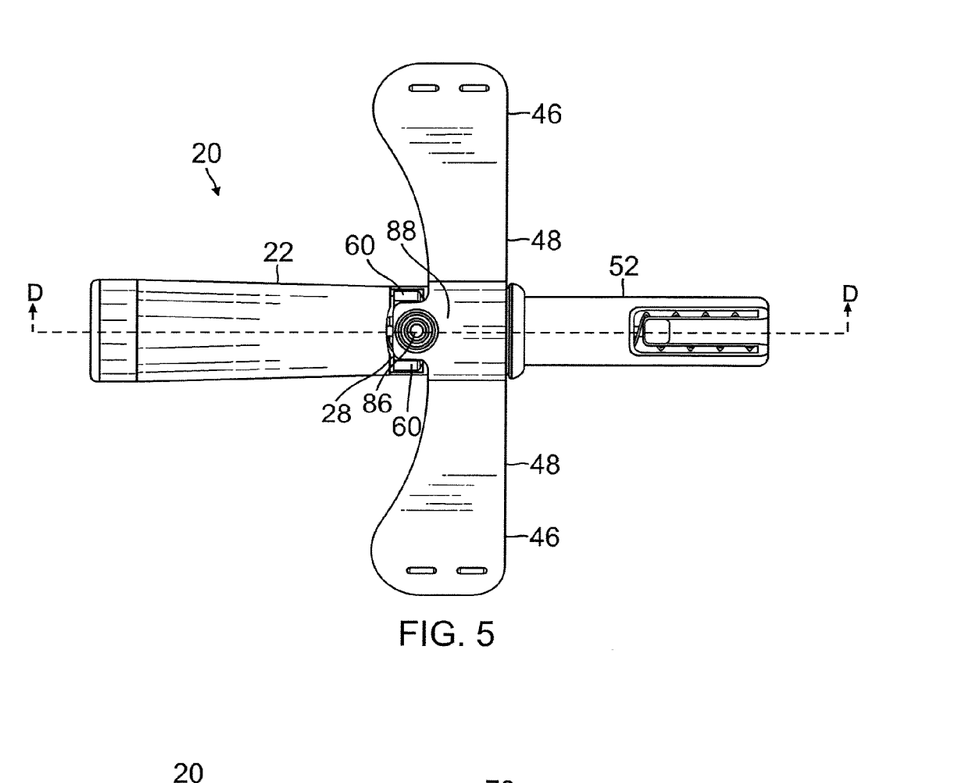
FIG. 5 is a top plan view of the safety needle assembly of FIG. 1 in a protected configuration.
Figure 6:
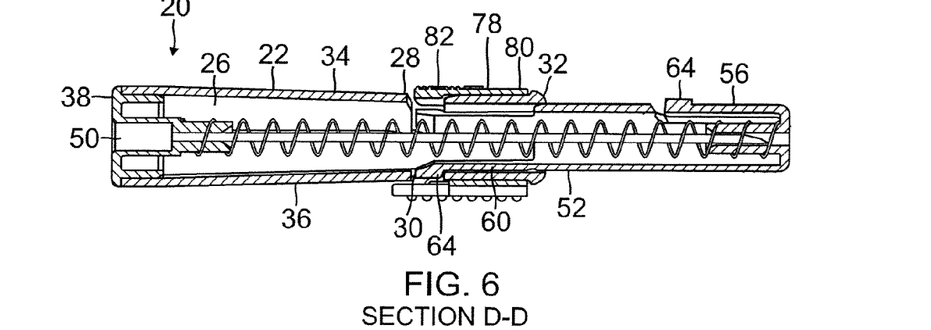
FIG. 6 is a left-side sectional view of the safety needle assembly of FIG. 5, taken through the line D-D in FIG. 5.

FIGS. 1-7 illustrate one embodiment of the present safety needle assembly 20. The assembly 20 is configured for use in withdrawing blood from a patient and/or infusing fluids to the patient, as described in detail below. FIGS. 1-4 illustrate the assembly 20 in a ready-to-use configuration in which a sharp distal tip 44 of a needle 42 is exposed. FIGS. 5 and 6 illustrate the assembly 20 in a protected configuration in which a needle shield 52 covers the sharp distal tip 44 of the needle 42. The principles of operation for converting the assembly 20 from the ready-to-use configuration to the protected configuration are described in detail below.

Figure 1:
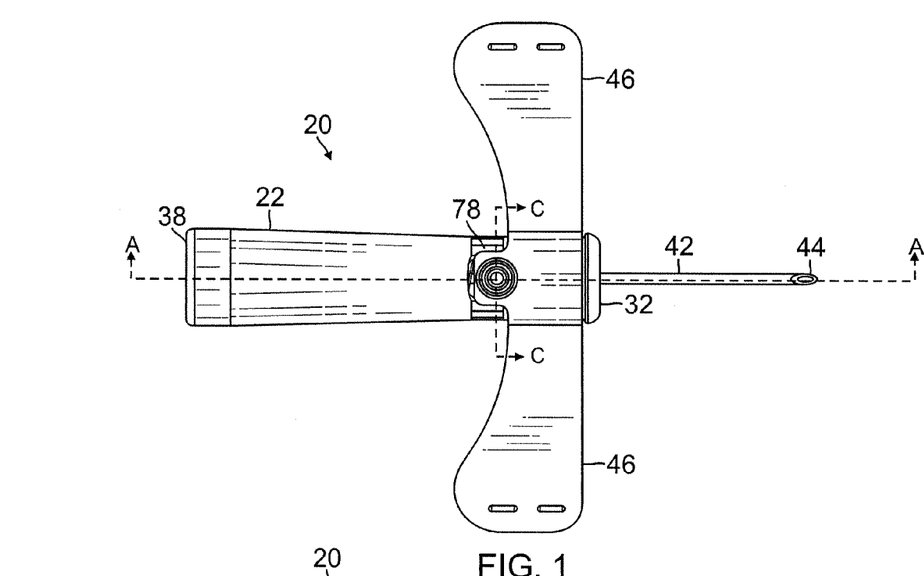
FIG. 1 is a top plan view of one embodiment of the present safety needle assembly in a ready-to-use configuration.
Figure 7:
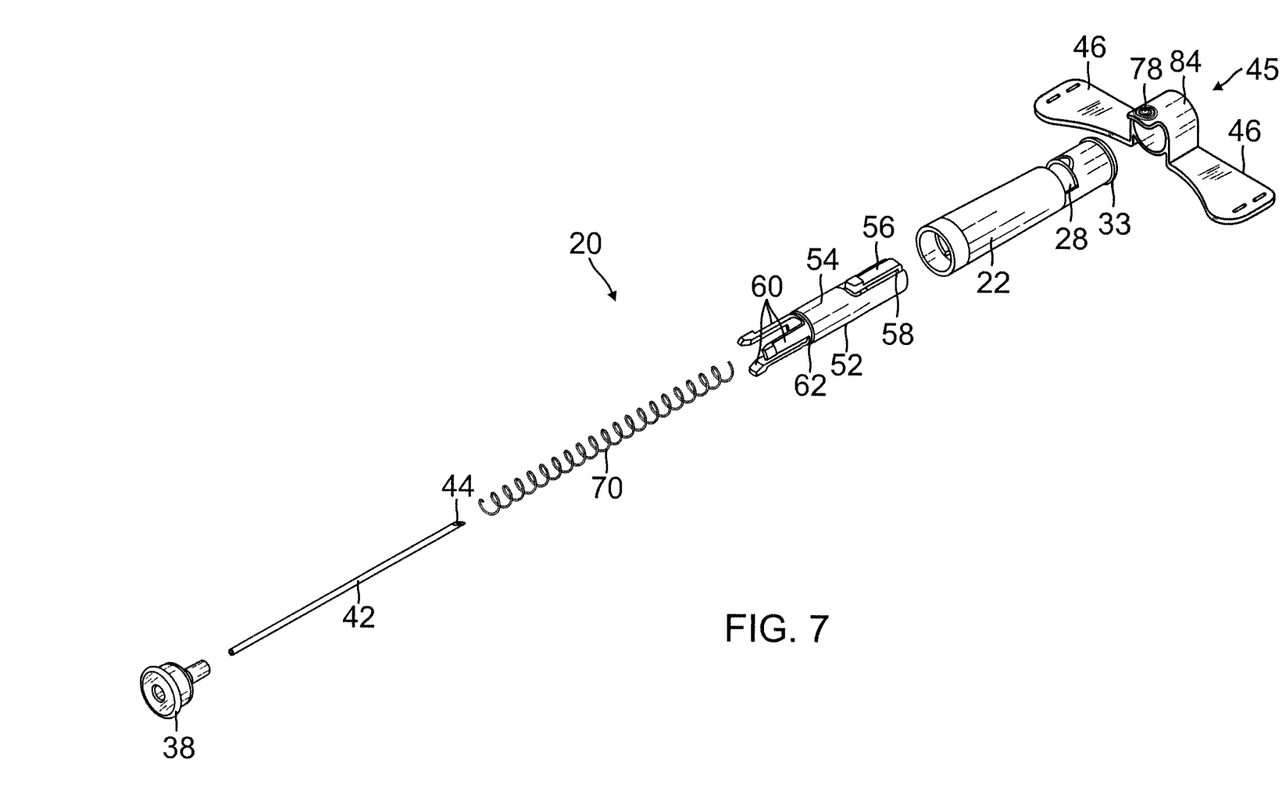
FIG. 7 is an exploded rear perspective view of the safety needle assembly of FIG. 1.

With reference to FIGS. 1, 3 and 7, the assembly 20 comprises an elongate body 22 including a body wall 24 defining an internal passageway 26 (FIGS. 3 and 6). The body wall 24 includes two openings 28, 30 toward a distal end 32 of the body 22. A first opening 28 is in an upper surface 34 of the body wall 24 and a second opening 30 is in a lower surface 36 of the body wall 24. The two openings 28, 30 oppose one another, but in alternative embodiments they may not and/or there may be more than two openings. Further, the first opening 28 extends almost halfway around the circumference of the body wall 24, but in alternative embodiments it may extend a lesser distance or a greater distance around the body wall 24. In certain embodiments the body 22 is fabricated as one piece. For example, the body 22 be constructed of an injection molded plastic such as polycarbonate, acrylonitrile butadiene styrene (ABS) or polystyrene plastic.

With reference to FIGS. 1, 3 and 7, a needle hub 38 engages a proximal end 40 of the body 22. In certain embodiments the needle hub 38 is stationary with respect to the body 22. For example, the needle hub 38 may engage the body 22 in a tight friction fit or a snap fit and/or it may be adhered, bonded, or welded to the body 22. A needle 42 extends distally from the needle hub 38 and through the body 22 internal passageway 26. The needle 42 includes a sharp distal tip 44 configured to pierce a patient's skin and vasculature.

With reference to FIGS. 1, 5 and 7, first and second wings 46 extend laterally in opposite directions from the body 22. Each wing 46 includes a substantially planar portion 48 configured to lie against a patient's skin. In certain embodiments the wings 46 are constructed of flexible material to enable them to follow contours on the patient's body or folded so that they touch one another for use during venipuncture. Non-limiting example materials include polyvinylchloride, low-density polyethylene, or thermoplastic elastomers such as KRATON®. Adhesive tape (not shown) overlapping the wings 46 and adhering to the patient's skin secures the assembly 20 to the patient, with the body 22 extending along the patient's skin. With the needle 42 disposed within the patient's vasculature and the wings 46 secured to the patient's skin, the assembly 20 is configured to engage apparatus (not shown) for withdrawing blood from the patient and/or infusing fluids to the patient. In the illustrated embodiment, for example, the needle hub 38 includes a recess 50 (FIG. 6) in fluid communication with the cannula (not shown) of the needle 42 and configured to receive a first and of a tube (not shown). A luer fitting or blood tube connector (not shown) may be attached to the second end of the tube. In alternative embodiments the needle hub 38 may be configured with a luer fitting to eliminate the need for a tube.

With reference to FIGS. 5-7, the assembly 20 further comprises a needle shield 52. In the ready-to-use configuration (FIGS. 1 and 3) the needle shield 52 is disposed within the body internal passageway 26 and surrounds a portion of the needle 42. The needle shield 52 is slidable in the axial direction with respect to the body 22 and with respect to the needle 42, as described in further detail below. With particular reference to FIG. 7, the needle shield 52 comprises a body portion 54 configured to be received within the body 22. A release latch 56 extends along the body portion 54 near a distal end 58 thereof, and three retention latches 60 extend from a proximal end 62 of the body portion 54. As shown, the three retention latches 60 are evenly spaced along a periphery of the safety shield and the release latch 56 is formed as a cut-out in or on the body portion 54 of the needle shield to form an elongated leg that flexes. With reference to FIG. 6, each of the latches 56, 60 comprises a leaf spring having a detent 64 adjacent one end. In certain embodiments the needle shield 52 and latches 56, 60 are fabricated as one piece. For example, the needle shield 52 and latches 56, 60 may be constructed of an injection molded plastic such as polypropylene, polyethylene or nylon. In other embodiments, the needle shield may be co-molded or over-molded from two or more different pieces.

The latches 56, 60 are configured to cooperate with the openings 28, 30 in the body wall 24 to restrict movement of the needle shield 52 with respect to the body 22, as described in further detail below. With reference to FIG. 4, an inner surface 66 of the body wall 24 includes channels 68 in which the retention latches 60 ride during relative axial movement of the needle shield 52 and the body 22. Interaction of the detents 64 with the channels 68 restricts relative rotation of the body 22 and the needle shield 52. In certain embodiments the needle shield 52 may be substantially not rotatable with respect to the body 22. This configuration facilitates alignment so that the latches 56, 60 engage the openings 28, 30 when the assembly is in the protected position, as further discussed below.

With reference to FIGS. 3 and 7, a biasing element 70 engages the needle shield 52 and biases the needle shield 52 toward the distal end 44 of the needle 42. In the illustrated embodiment, the biasing element 70 is a coil spring. However, those of ordinary skill in the art will appreciate that the biasing element 70 could comprise alternative apparatus, such as an elastic accordion-type sleeve. A proximal end 72 of the biasing element 70 engages the needle hub 38 and a distal end 74 of the biasing element 70 engages the needle shield 52 (FIG. 3). The needle hub 38 and the needle shield 52 each include a stem or post 76 configured to support the ends 72, 74 of the biasing element 70. In the ready-to-use configuration of FIG. 3 the biasing element 70 is in compression. The biasing element 70 may be constructed of any suitable material, such as one or more metals or plastic including, without limitation, steel, stainless steel and copper alloy or nylon.

Figure 2:
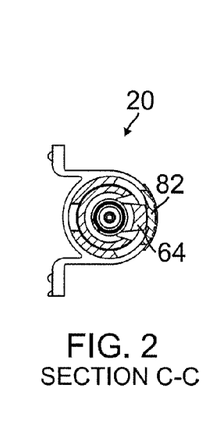
FIG. 2 is a rear sectional view of the safety needle assembly of FIG. 1, taken through the line C-C in FIG. 1.

With continued reference to FIG. 3, in the ready-to-use configuration the detent 64 on the release latch 56 engages an edge of the first opening 28 in the body wall 24. The engagement prevents movement of the needle shield 52 distally with respect to the body 22 and with respect to the needle 42 to thereby compress the biasing element 70 between the two posts 76. A portion of a push button activator 78 overlies the detent 64, as shown in FIGS. 2 and 3, With reference to FIG. 6, the push button activator 78 includes a portion 80 that engages an outer surface of the body wall 24 and a cantilevered portion 82 extending across the first opening 28 in the body wall 24. With particular reference to FIG. 7, in the illustrated embodiment the push button activator 78 further comprises a sleeve portion 84 that fits around the outer surface of the body wall 24 and is formed integrally (as one piece) with the wings 46. Those of ordinary skill in the art will appreciate that the push button activator 78 could have other configurations, such as a multi-piece construction.

One aspect of the present embodiments comprises a wing assembly 45 (FIG. 7) including a cylindrical sleeve 84 disposed between two generally planar wings 46 and having a cantilevered portion 82 extending from the sleeve 84. In a particular aspect of this embodiment, the sleeve 84 is wedged between a lip 33 (FIG. 3) near the distal end 32 of the body 22 and an opening 28 in the body wall 24. The cantilevered portion 82 couples with the opening 28 to axially and rotationally fix the wing assembly 45 relative to the body 22. In other embodiments the needle assembly 20 may not include the wing assembly 45 or the push button activator 78, which, as shown, extends proximally.

With reference to FIGS. 2 and 3, the cantilevered portion 82 of the push button activator 78 abuts or is positioned adjacent the detent 64 of the release latch 56. Digital pressure applied to the push button activator 78 is thus transmitted to the detent 64. Sufficient applied digital pressure disengages the detent 64 from the edge of the first opening 28 in the body wall 24. In an embodiment without a wing assembly, digital pressure applied directly to the detent 64 may disengage it from the opening 28. Once disengaged, the stored energy in the biasing element 70 is released and the biasing element 70 pushes the needle shield 52 distally with respect to the body 22 and with respect to the needle 42 and into the protected configuration shown in FIGS. 5 and 6. With reference to FIG. 5, an outer surface of the push button activator 78 may include surface features 86 that reduce slippage of the operator's thumb or finger and/or indicia 88 indicating to the operator where digital pressure should be applied.

With reference to FIGS. 5 and 6, the stored energy in the biasing element 70 forces the needle shield 52 into the protected configuration once the detent 64 on the release latch 56 disengages the first opening 28. The retention latches 60 slide within the grooves 68 in the inner surface 66 of the body wall 24 (FIG. 4). As the needle shield 52 approaches the protected configuration, the detents 64 on the retention latches 60 approach the openings 28, 30 in the body wall 24. The body wall 24 tapers down from its proximal end 40 to its distal end 32 (FIG. 3). Thus, as the needle shield 52 moves distally from the ready-to-use configuration to the protected configuration the inner surface of the body wall 24 biases the leaf spring retention latches 60 inward. When the detents 64 of the retention latches 60 reach the openings 28, 30 in the body wall 24 they snap outward and engage the edges of the openings 28, 30, halting further distal movement of the needle shield 52. With reference to FIGS. 5 and 6, two of the retention latches 60 catch in the first opening 28, and the third retention latch 60 catches in the second opening 30. Those of ordinary skill in the art will appreciate that the present assembly 20 could have any number of retention latches and body wall openings. The illustrated embodiment is not limiting. Advantageously, the detents 64 of the retention latches 60 also prevent re-exposure of the sharp distal tip 44 of the needle 42. Edges of the openings 28, 30 provide barriers for the detents 64 that prevent the needle shield 52 from being pushed back proximally into the body 22 far enough to expose the sharp distal tip 44 (FIG. 6). Additionally, the sleeve portion 84 covers the detents 64 to deter manipulation by a user in attempting to re-use the needle assembly.

One aspect of the present embodiments includes inwardly biasing a plurality of retention latches 60 as they move from a proximal position to a distal position within a body 22 to create outward resilient forces so that detents 64 located on the retention latches 60 positively latch against corresponding mating detents, such as two openings 28, 30.

The safety needle assembly 20 illustrated in FIGS. 1-7 is advantageously ergonomic. With reference to FIG. 1, the body 22 is sized and shaped to enable an operator to grip it easily with one hand. The push button activator 78 is positioned on a top side of the body 22 adjacent the distal end 32. The push button activator 78 is thus positioned so that an operator gripping the body 22 can easily reach the push button activator 78 with the thumb or forefinger on the same hand. Further, the assembly 20 does not include any moving parts that interfere with the operator's grip on the body 22. Thus, holding the body 22 with one hand and depressing the push button activator 78, the assembly 20 transitions from the ready-to-use configuration to the protected configuration without the need for the operator to move his gripping hand or use his other hand. Thus, aspects of the present embodiments include manufacturing a safety needle assembly having ergonomic features. One such embodiment comprises forming an elongated body having a plurality of openings and positioning a needle hub having a needle attached thereto in an interior cavity of the elongated body. A biasing member is compressed in between the needle hub and a needle shield assembly comprising a plurality of proximally extending arms, wherein each arm comprises a detent. The needle shield is coaxially disposed over the needle and is movable to cover the sharp tip of the needle. The needle shield assembly comprises a release latch engaged to one of the plurality of openings. A wing assembly is mounted over the elongated body with a cantilevered portion provided for disengaging the release latch from the opening. The assembly has a conveniently located push button and has two resilient forces acting on the needle shield, namely an axially directed force provided by a resilient member, such as a coil spring, and a radially directed force provided by a leaf spring, such as a cantilevered release latch.

Figure 8:
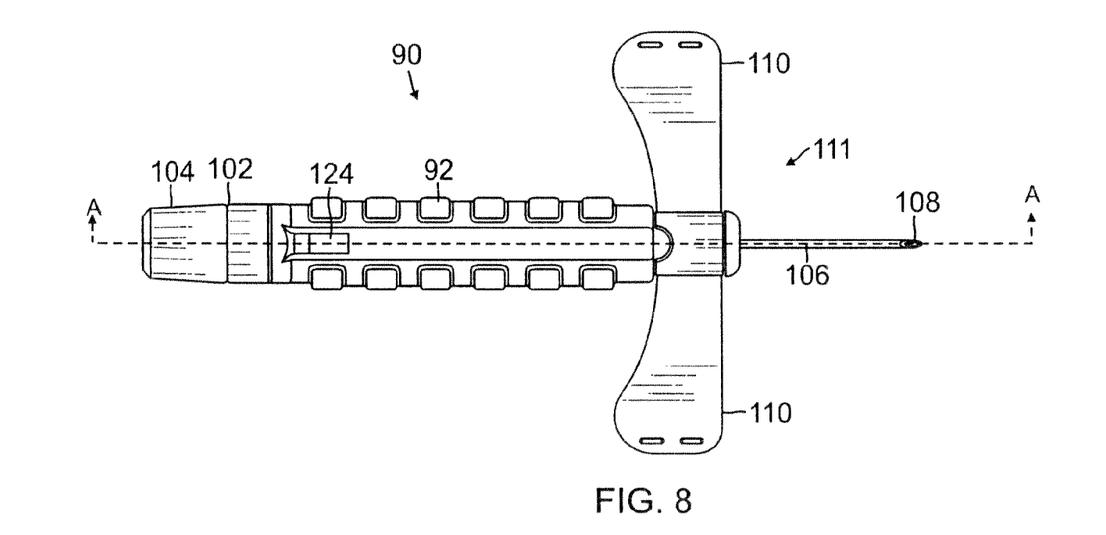
FIG. 8 is a top plan view of another embodiment of the present safety needle assembly in a ready-to-use configuration.
Figure 9:
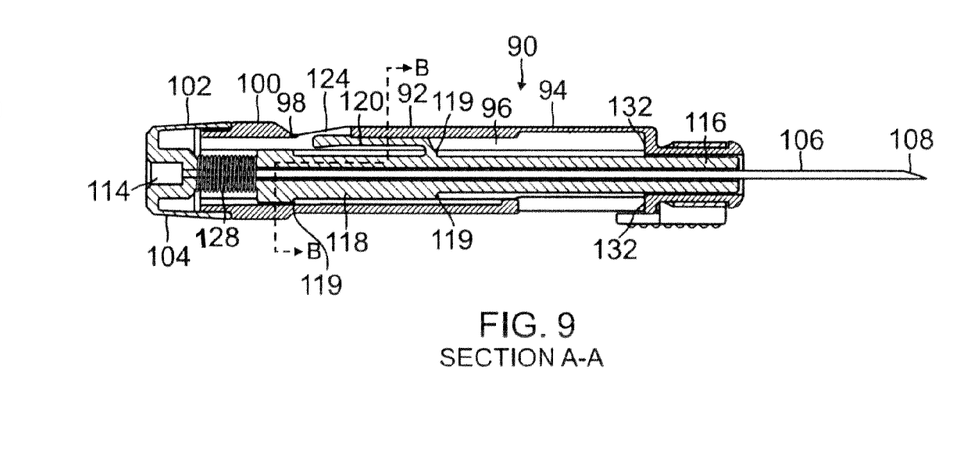
FIG. 9 is a left-side sectional view of the safety needle assembly of FIG. 8, taken through the line A-A in FIG. 8.
Figure 10:
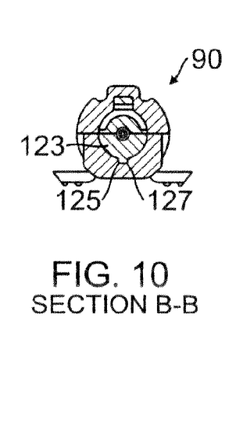
FIG. 10 is a rear sectional view of the safety needle assembly of FIG. 8, taken through the line B-B in FIG. 9.
Figure 11:
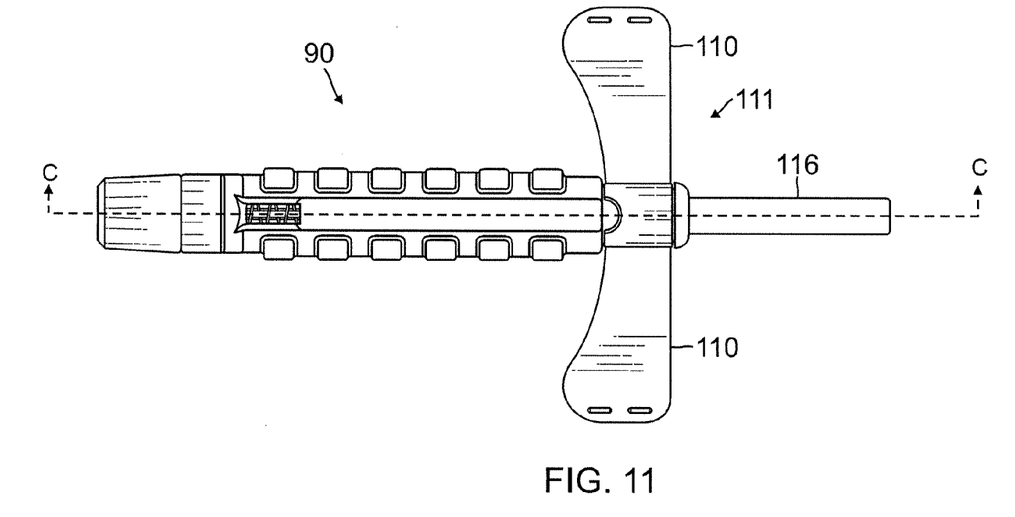
FIG. 11 is a top plan view of the safety needle assembly of FIG. 8 in a protected configuration.
Figure 12:
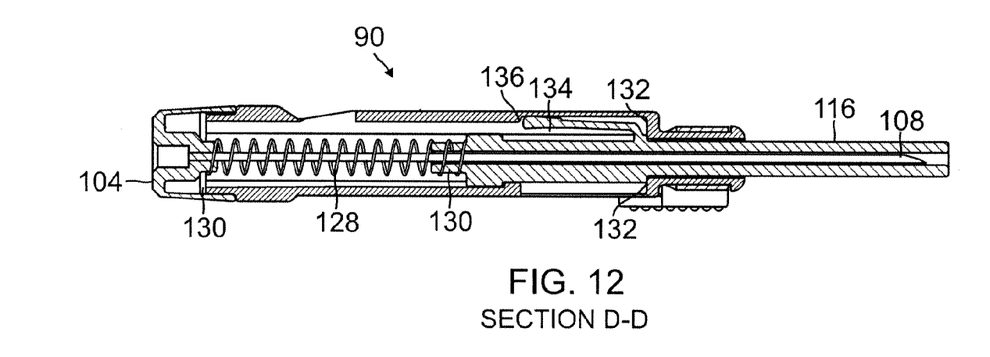
FIG. 12 is a left-side sectional view of the safety needle assembly of FIG. 11, taken through the line C-C in FIG. 11.

FIGS. 8-13 illustrate another embodiment of the present safety needle assembly 90. The assembly 90 is configured for use in withdrawing blood from a patient and/or infusing fluids to the patient, as described in detail below. FIGS. 8-10 illustrate the assembly 90 in a ready-to-use configuration in which a sharp distal tip 108 of the needle 106 is exposed. FIGS. 11 and 12 illustrate the assembly 90 in a protected configuration in which a needle shield 116 covers the sharp distal tip 108 of the needle 106. The principles of operation for converting the assembly 90 from the ready-to-use configuration to the protected configuration are described in detail below.

Figure 13:
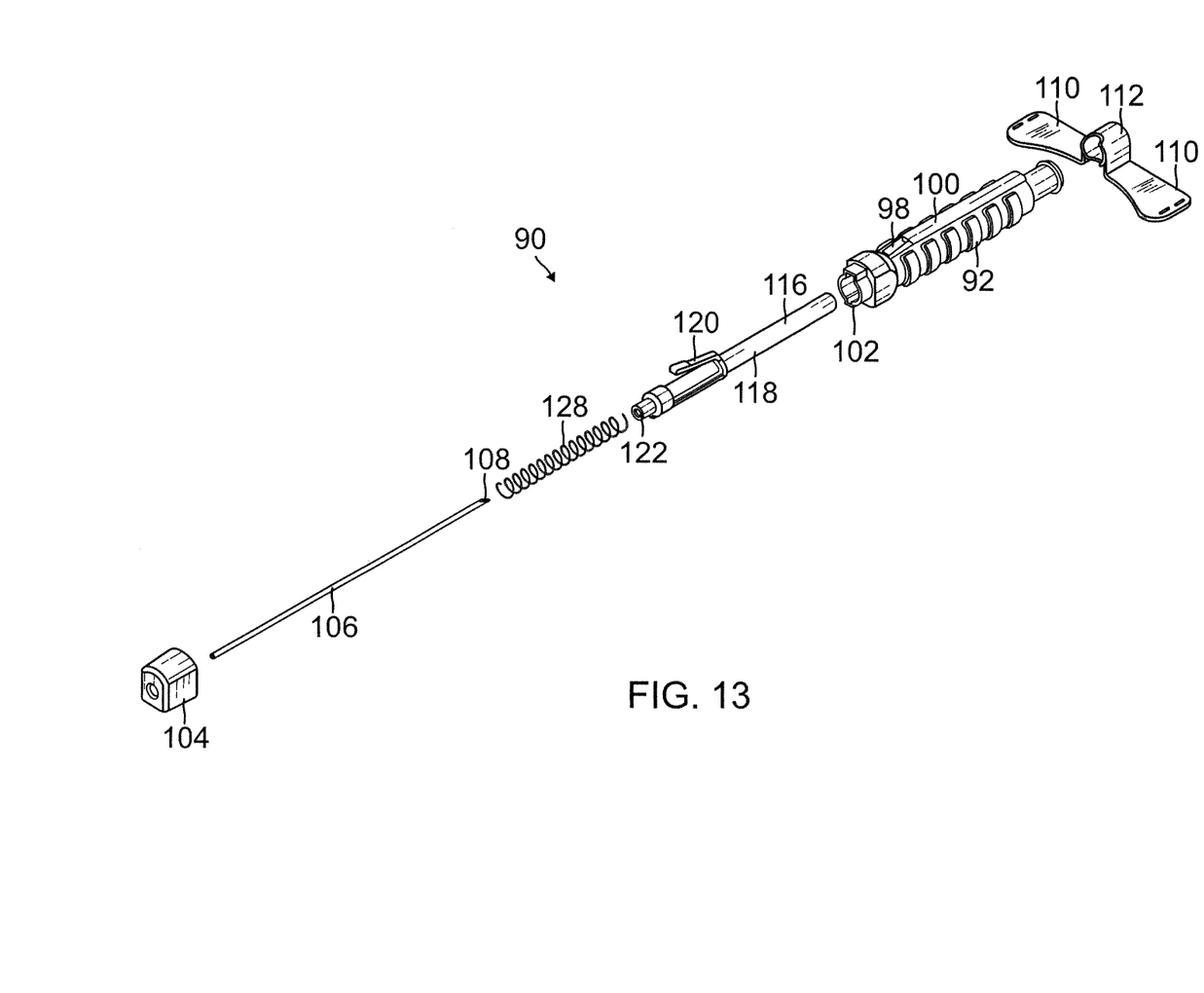
FIG. 13 is an exploded rear perspective view of the safety needle assembly of FIG. 8.

With reference to FIGS. 8, 9 and 13, the assembly 90 comprises an elongate body 92 including a body wall 94 defining an internal passageway 96 (FIG. 9). The body wall 94 includes an opening 98 in an upper surface 100 toward a proximal end 102 of the body 92. In certain embodiments the body 92 is fabricated as one piece. For example, the body 92 may be constructed of an injection molded plastic such as polycarbonate, acrylonitrile butadiene styrene (ABS) or polystyrene plastic.

With reference to FIGS. 8, 9 and 13, the needle hub 104 engages the proximal end 102 of the body 92. In certain embodiments the needle hub 104 is stationary with respect to the body 92. For example, the needle hub 104 may engage the body 92 in a tight friction fit or a snap fit and/or it may be adhered or welded to the body 92. A needle 106 extends distally from the needle hub 104 and through the body 92 internal passageway 96. The needle 106 includes a sharp distal tip 108 configured to pierce a patient's skin and vasculature.

With reference to FIGS. 8, 11 and 13, first and second wings 110 of a wing assembly 111 extend laterally in opposite directions from the body 92. The structure and function of the wings 110 is substantially similar to the wings 46 described above with respect to FIGS. 1-7. However, with particular reference to FIG. 13, in the illustrated embodiment the wings 110 include a sleeve portion 112 that fits around the outer surface of the body wall 94 and is formed integrally (as one piece) with the wings 110. Unlike the wings 46 and sleeve portion 84 of FIGS. 1-7, however, the sleeve portion 112 does not include a push button activator. Further, those of ordinary skill in the art will appreciate that the wings 110 could have other configurations, such as a multi-piece construction or wings that fold, such as by incorporating living hinges.

With the needle 106 disposed within the patient's vasculature and the wings 110 secured to the patient's skin, the assembly 90 is configured to engage apparatus (not shown) for withdrawing blood from the patient and/or infusing fluids to the patient. In the illustrated embodiment, for example, the needle hub 104 includes a recess 114 (FIG. 9) in fluid communication with the cannula (not shown) of the needle 106 and configured to receive a first end of a tube (not shown). A luer fitting or blood tube connector (not shown) may be attached to the second end of the tube. In alternative embodiments the needle hub 104 may be configured with a luer fitting to eliminate the need for a tube.

With reference to FIGS. 9, 11, 12 and 13, the assembly 90 further comprises a needle shield 116. In the ready-to-use configuration (FIG. 9) the needle shield 116 is disposed within the body internal passageway 96 and surrounds a portion of the needle 106. The needle shield 116 is slidable in the axial direction with respect to the body 92 and with respect to the needle 106, as described in further detail below.

With particular reference to FIG. 13, the needle shield 116 comprises a body portion 118 configured to be received within the body 92. A release latch 120 extends along the body portion 118 near a proximal end 122 thereof. The release latch 120 comprises a leaf spring having a detent 124 adjacent one end (FIG. 9). With reference to FIGS. 8 and 9, the detent 124 is configured to cooperate with the opening 98 in the body wall 94 to restrict movement of the needle shield 116 with respect to the body 92, as described in further detail below. In certain embodiments the needle shield 116 and latch are fabricated as one piece. For example, the needle shield 116 and latch may be constructed of an injection molded plastic such as polypropylene, polyethylene or nylon.

With particular reference to FIG. 9, the needle shield body portion 118 further comprises a stepped configuration, having portions of different diameters along its length, with each portion separated from its neighboring portion by a step 119. With reference to FIG. 10, a relatively large diameter proximal portion 123 of the needle shield 116 includes a tongue 125 that engages a groove 127 in the inner surface of the body wall 94 to guide the sliding movement of the needle shield 116 and to prevent relative rotation of the needle shield 116 and the body 92.

With reference to FIGS. 9, 12 and 13, a biasing element 128 engages the needle shield 116 and biases the needle shield 116 toward a distal end of the needle 106. In the illustrated embodiment, the biasing element 128 is a coil spring. However, those of ordinary skill in the art will appreciate that the biasing element 128 could comprise alternative apparatus, such as an elastic accordion-type sleeve. A proximal end of the biasing element 128 engages the needle hub 104 and a distal end of the biasing element 128 engages the needle shield 116. The needle hub 104 and the needle shield 116 each include a stem 130 (FIG. 12) configured to support the ends of the biasing element 128. In the ready-to-use configuration of FIG. 9 the biasing element 128 is in compression. The biasing element 128 may be constructed of any suitable material, such as one or more metals or plastic including, without limitation, steel, stainless steel and copper alloy or nylon.

With continued reference to FIG. 9, in the ready-to-use configuration the detent 124 on the release latch 120 engages an edge of the opening 98 in the body wall 94. The engagement prevents movement of the needle shield 116 distally with respect to the body 92 and with respect to the needle 106. Digital pressure applied to the detent 124 disengages the detent 124 from the edge of the opening 98 in the body wall 94. Once disengaged, the stored energy in the biasing member is released and the needle shield 116 moves distally with respect to the body 92 and with respect to the needle 106 and into the protected configuration shown in FIGS. 11 and 12.

With reference to FIGS. 9 and 12, the stored energy in the biasing member forces the needle shield 116 into the protected configuration once the detent 124 on the release latch 120 disengages the opening 98. As the needle shield 116 approaches the protected configuration, the most distal steps 119 on the needle shield 116 approach a distal wall 132 of the body 92. When the steps 119 reach the distal wall 132, further distal movement of the needle shield 116 is halted. In the protected configuration of FIG. 12 the sharp distal tip 108 of the needle 106 is advantageously covered to prevent needle-sticks.

With continued reference to FIG. 12, the body 92 further includes a release latch receiving space 134 toward a distal end thereof. As the needle shield 116 moves from the ready-to-use configuration to the protected configuration the body wall 94 biases the release latch 120 leaf spring inward. When the needle shield 116 reaches the protected configuration the release latch 120 pops up into the release latch receiving space 134. A proximal wall 136 of the receiving space 134 provides a barrier for the release latch 120 that restricts proximal movement of the needle shield 116 with respect to the needle 106. The barrier prevents the needle shield 116 from being pushed back proximally into the body 92 far enough to expose the sharp distal tip 108.

Figure 18:
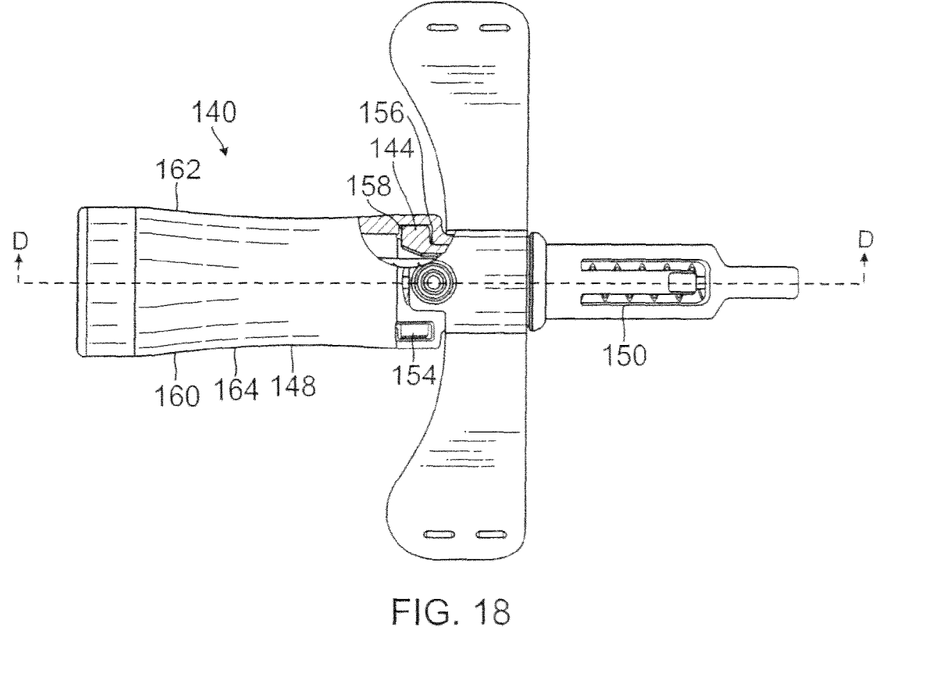
FIG. 18 is a top plan view of the safety needle assembly of FIG. 14 in a protected configuration.
Figure 19:
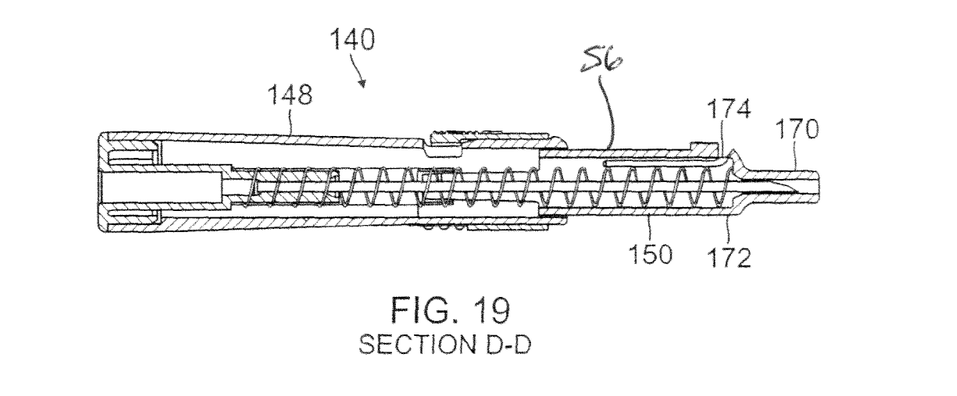
FIG. 19 is a left-side sectional view of the safety needle assembly of FIG. 18, taken through the line D-D in FIG. 18.
Figure 20:
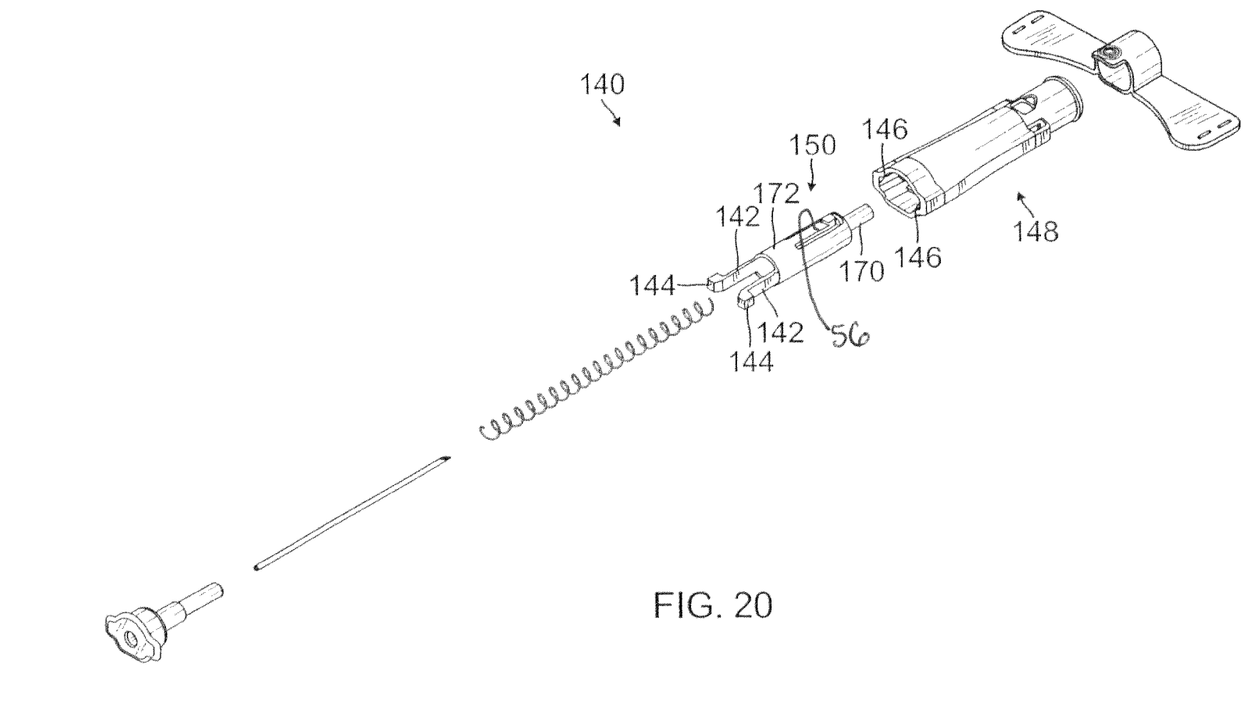
FIG. 20 is an exploded rear perspective view of the safety needle assembly of FIG. 14.

FIGS. 14-20 illustrate another embodiment of the present safety needle assembly 140. The structure and operation of the safety needle assembly 140 of FIGS. 14-20 is similar to that of the safety needle assembly 20 of FIGS. 1-7. The assembly 140 of FIGS. 14-20, however, includes two retention latches 142 (FIG. 20) instead of three. In one embodiment, the latches 142 are diametrically opposed, and each comprises a leaf spring having a detent 144 adjacent one end. As shown in FIG. 20, each leaf spring is embodied as a leg 175 extending from the proximal end of the proximal elongated section 172 and having the detent 144 at an end thereof.

Figure 17:
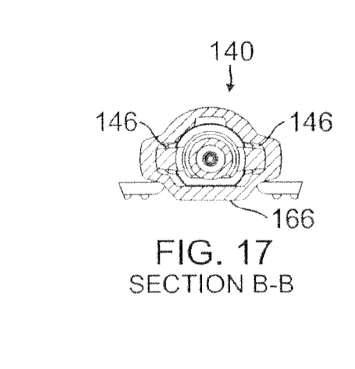
FIG. 17 is a rear sectional view of the safety needle assembly of FIG. 14, taken through the line B-B in FIG. 16.

The latches 142 are configured to slide within two diametrically opposed channels 146 (FIGS. 17 and 20) in the body 148 of the assembly 140, when the needle shield 150 moves from the ready-to-use configuration of FIGS. 14-17 to the protected configuration of FIGS. 18 and 19. In one embodiment, the needle shield 150 has a distal elongated section 170 of a first diameter and a proximal elongated section 172 of a second diameter. In a particular embodiment, the first diameter is less than the second diameter. In another embodiment, the distal elongated section 170 defines an distal internal channel sized to accommodate a needle and the proximal elongated section 172 defines a proximal internal channel sized to accommodate a spring, which internal dimension is larger than the distal internal channel. A shoulder 174 (FIG. 19) located between the two sections provide a physical stop for a spring.

As in the embodiment of FIGS. 1-7, inner surfaces 152 (FIG. 14) of the channels 146 taper inwardly in the proximal-to-distal direction such that one surface of one channel to the other is closer in the distal direction than in the proximal direction. Thus, as the needle shield 150 moves from the ready-to-use configuration to the protected configuration, the retention latches 142 bow inwardly due to the more closely spaced wall surfaces until the detents 144 reach cavities 154 (FIGS. 14 and 18) in the interior of the body 148 at the distal ends of the channels 146. In a particular embodiment, the cavities are visible from the exterior surface through openings positioned subjacent and superjacent each cavity. In practice, the openings are incorporated for molding the cavities at the corresponding ends of the two channels 146. Other similar and corresponding features of FIGS. 1-7 are understood to apply equally to the assembly of FIGS. 14-20. For example, although certain shown features are not separately labeled, they are understood to be similar to those corresponding features in FIGS. 1-7.

When the detents 144 reach the cavities 154, the forces applied to the latches 142 by the inner surfaces 152 of the channels 146 are released, and the detents 144 "pop" outward into the cavities 154. Engagement of the detents 144 with the distal walls 156 (FIG. 18) of the cavities 154 prevents the needle shield 150 from advancing any farther than as shown in FIG. 18. Engagement of the detents 144 with the proximal walls 158 (FIG. 18) of the cavities 154 prevents the needle shield 150 from being retracted into the body 148.

Figure 14:
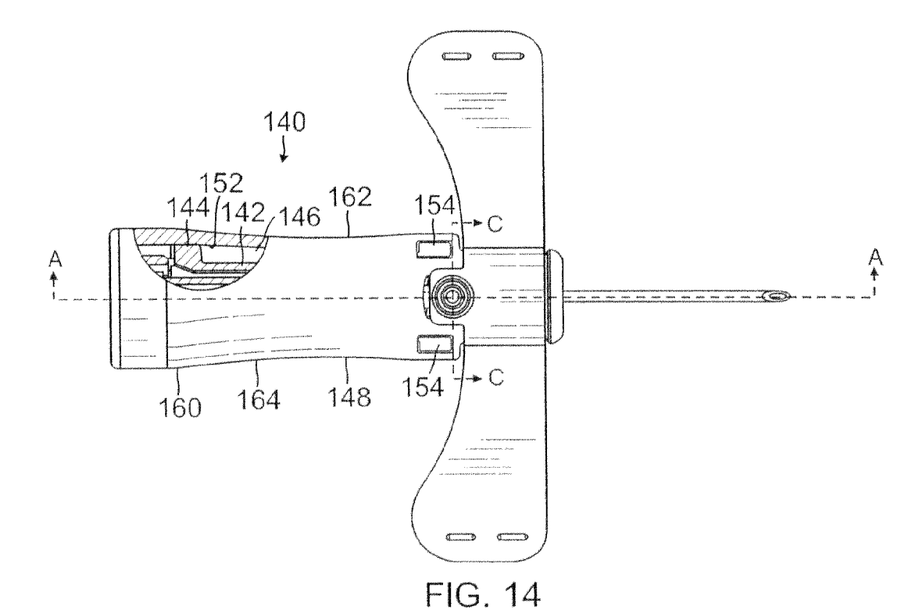
FIG. 14 is a top plan view of another embodiment of the present safety needle assembly in a ready-to-use configuration.

With reference to FIGS. 14 and 18, an outer surface 160 of the body 148 of the safety needle assembly 140 includes contours on its left and right sides 162, 164. The contours provide the body 148 with an hourglass appearance in top plan view. The contours provide a comfortable and secure grip for the operator.

Figure 15:
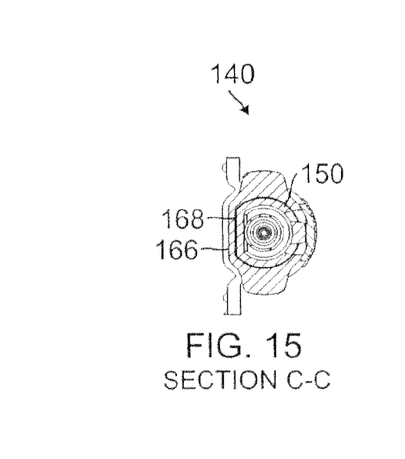
FIG. 15 is a rear sectional view of the safety needle assembly of FIG. 14, taken through the line C-C in FIG. 14.
Figure 16:
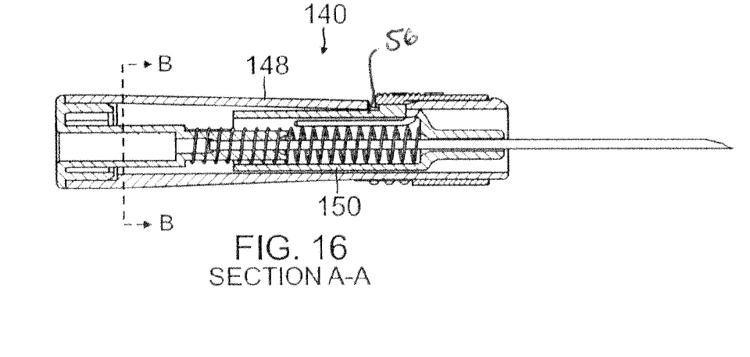
FIG. 16 is a left-side sectional view of the safety needle assembly of FIG. 14, taken through the line A-A in FIG. 14.

With reference to FIGS. 15 and 17, lower surfaces 166, 168 of the body 148 and the needle shield 150 are flat. The abutting flat surfaces 166, 168 advantageously prevent relative rotation of the body 148 and the needle shield 150. Further, the flat outer surface 166 of the body 148 advantageously provides the safety needle assembly 140 with a low profile. During venipuncture, the assembly 140 can thus be positioned relative to the patient at a relatively flat angle (approaching parallel to the patient's body surface). After the vasculature has been punctured, the assembly 140 is secured to the patient with adhesive tape as described above. The assembly 140 thus lies relatively flat against the patient's skin.

The above description presents the best mode contemplated for carrying out the present safety needle assembly and methods, and of the manner and process of making and using it, in such full, clear, concise, and exact terms as to enable any person skilled in the art to which it pertains to make and use this safety needle assembly and methods. This safety needle assembly and methods is, however, susceptible to modifications and alternate constructions from that discussed above that are fully equivalent. Consequently, this safety needle assembly and methods is not limited to the particular embodiments disclosed. On the contrary, this safety needle assembly and methods covers all modifications and alternate constructions coming within the spirit and scope of the safety needle assembly and methods as generally expressed by the following claims, which particularly point out and distinctly claim the subject matter of the safety needle assembly and methods. Still furthermore, it is contemplated that features or structures discussed specifically with respect to one embodiment may be included in another embodiment provided the features or structures are compatible for use in the other embodiment.

What is claimed is:
1. A safety needle assembly, comprising:
an elongate body including a body wall defining an internal passageway and including an opening in the body wall;
a needle hub engaging a proximal end of the body and being stationary with respect to the body;
a needle extending distally from the needle hub and through the body internal passageway, the needle including a sharp distal tip;
a needle shield disposed within the body internal passageway and surrounding a portion of the needle, the needle shield being slidable with respect to the body and with respect to the needle and having a body portion compris- ing a proximal end having a proximal opening with at least one retention latch extending from the proximal end of the needle shield;
a biasing element engaging the needle shield and biasing the needle shield toward a distal end of the needle; and
a release latch extending from the needle shield, the release latch comprising a leaf spring formed as a cut-out on the body portion of the needle shield having a detent located thereon;
wherein when the assembly is in a ready-to-use configuration, the detent on the release latch engages an edge of the opening in the body wall and prevents movement of the needle shield distally with respect to the body and with respect to the needle, and further wherein digital pressure applied to the release latch disengages the detent from the edge of the opening in the body wall and enables movement of the needle shield distally with respect to the body and with respect to the needle.

2. The safety needle assembly of claim 1, further comprising a wing extending laterally from the body, the wing including a substantially planar portion configured to lie against a patient's skin for securing the assembly to a patient.

3. The safety needle assembly of claim 2, further comprising a push button activator attached to the wing and engaging an outer surface of the body wall and including a cantilevered portion extending across the opening in the body wall.

4. The safety needle assembly of claim 3, wherein when the assembly is in the ready-to-use configuration the cantilevered portion of the push button activator engages the detent so that digital pressure applied to the push button is transmitted to the detent.

5. The safety needle assembly of claim 1, wherein the biasing element is a coil spring.

6. The safety needle assembly of claim 1, wherein a proximal end of the biasing element engages the needle hub and a distal end of the biasing element engages the needle shield.

7. The safety needle assembly of claim 1, further comprising a second retention latch extending from the needle shield.

8. The safety needle assembly of claim 7, wherein when the assembly is in a protected configuration in which the needle shield covers the needle distal tip, the at least one retention latch engages a second opening in the body wall to prevent the needle shield from being completely discharged from the body through the distal end thereof.

9. The safety needle assembly of claim 7, wherein when the assembly is in a protected configuration in which the needle shield covers the needle distal tip, the at least one retention latch engages a second opening in the body wall to prevent the needle shield from sliding proximally with respect to the needle and exposing the needle distal tip.

10. The safety needle assembly of claim 7, wherein when the assembly is in a protected configuration in which the needle shield covers the needle distal tip, the at least one retention latch engages a cavity in the body to prevent the needle shield from being completely discharged from the body through the distal end thereof.

11. The safety needle assembly of claim 7, wherein when the assembly is in a protected configuration in which the needle shield covers the needle distal tip, the at least one retention latch engages a cavity in the body wall to prevent the needle shield from sliding proximally with respect to the needle and exposing the needle distal tip.

12. A method of shielding a needle in a safety needle assembly, the method comprising:
grasping an elongate body of the assembly in a ready-to-use configuration, the elongate body including a body wall defining an internal passageway and including an opening in the body wall, the internal passageway enclosing a portion of a needle having a sharp distal tip, the sharp distal tip extending beyond an open end of the body; and
depressing a release latch extending from a needle shield to thereby disengage a detent of the release latch from an edge of the opening in the body wall, disengagement of the detent from the opening releasing a compressive force on a biasing member and causing the needle shield disposed within the body internal passageway to slide distally with respect to the body and with respect to the needle and to cover the needle distal tip, the needle shield stops sliding distally when at least one retention latch extending from a proximal end of a body portion of the needle shield engages the elongate body;
wherein the needle is held in a needle hub that engages a proximal end of the elongate body and is stationary with respect to the elongate body, such that when the release latch is depressed neither the needle nor the needle hub moves with respect to the elongate body.

13. The method of claim 12, wherein the biasing member is a coil spring.

14. The method of claim 12, wherein depressing the release latch further comprises depressing a push button engaging an outer surface of the body wall and including a cantilevered portion extending across the opening in the body wall.

15. The method of claim 14, wherein when the assembly is in the ready-to-use configuration the cantilevered portion of the push button engages the detent so that digital pressure applied to the push button is transmitted to the detent.

16. The method of claim 12, wherein when the assembly is in a protected configuration in which the needle shield covers the needle distal tip, the at least one retention latch engages a second opening in the body wall to prevent the needle shield from being completely discharged from the body through the distal end thereof.

17. The method of claim 12, wherein when the assembly is in a protected configuration in which the needle shield covers the needle distal tip, the at least one retention latch engages a second opening in the body wall to prevent the needle shield from sliding proximally with respect to the needle and exposing the needle distal tip.

18. The method of claim 12, wherein when the assembly is in a protected configuration in which the needle shield covers the needle distal tip, the at least one retention latch engages a cavity in the body to prevent the needle shield from being completely discharged from the body through the distal end thereof.

19. The method of claim 12, wherein when the assembly is in a protected configuration in which the needle shield covers the needle distal tip, the at least one retention latch engages a cavity in the body to prevent the needle shield from sliding proximally with respect to the needle and exposing the needle distal tip.

20. A safety needle assembly comprising
an elongate body including a body wall defining an internal passageway and including an opening in the body wall;
a needle hub engaging a proximal end of the elongate body and being stationary with respect to the elongate body and having a needle extending distally from the needle hub and through the body internal passageway, the needle including a sharp distal tip;
a needle shield disposed within the body internal passageway and surrounding a portion of the needle, the needle shield being slidable with respect to the elongate body and with respect to the needle and having an elongated section having a proximal end with a proximal opening, an internal bore of a first diameter, a release latch comprising a leaf spring extending from the elongated section, and a plurality of retention latches, each comprising a leg and a detent extending from the proximal end of the elongated section;

a biasing element engaging the needle shield and biasing the needle shield toward a distal end of the needle; and wherein the release latch is engaged to the opening in the body wall to maintain the biasing element in a compressed state.

21. The safety needle assembly of claim 20, further comprising a wing assembly comprising an extending activator and wherein said extending activator is positioned adjacent said release latch.

22. The safety needle assembly of claim 20, wherein the proximally extending retention latches are evenly spaced along a periphery of the elongated section.

* * * * *

UNITED STATES PATENT AND TRADEMARK OFFICE
CERTIFICATE OF CORRECTION

Page 1 of 1

PATENT NO. : 8,439,870 B2
APPLICATION NO. : 12/555523
DATED : May 14, 2013
INVENTOR(S) : Scott A. Moyer et al.

It is certified that error appears in the above-identified patent and that said Letters Patent is hereby corrected as shown below:

On Title page, Item (75), in "Inventors", column 1, line 1, Delete "Breiningsville" and insert -- Breinigsville --, therefor.

In the Specification

In column 1, line 63, Delete "Co" and insert -- to --, therefor.

In column 2, line 18, Delete "huh" and insert -- hub --, therefor.

In column 3, line 34, Delete "atop" and insert -- a top --, therefor.

In column 4, line 17, After "22" insert -- may --.

In column 4, line 48, Delete "and" and insert -- end --, therefor. (second occurrence)

Signed and Sealed this
Twelfth Day of August, 2014

Michelle K. Lee
*Deputy Director of the United States Patent and Trademark Office*